(12) United States Patent
Saunois et al.

(10) Patent No.: US 8,957,232 B2
(45) Date of Patent: Feb. 17, 2015

(54) LIQUID/LIQUID EXTRACTION

(75) Inventors: Alex Saunois, Nogent-le-Roi (FR); Jacques Legrand, Neuilly sur Eure (FR); Eglantine Mercier, Rambouillet (FR)

(73) Assignee: Laboratoires Expanscience, Courbevoie (FR)

( * ) Notice: Subject to any disclaimer, the term of this patent is extended or adjusted under 35 U.S.C. 154(b) by 8 days.

(21) Appl. No.: 13/575,402

(22) PCT Filed: Jan. 31, 2011

(86) PCT No.: PCT/EP2011/051321
§ 371 (c)(1),
(2), (4) Date: Oct. 16, 2012

(87) PCT Pub. No.: WO2011/092329
PCT Pub. Date: Aug. 4, 2011

(65) Prior Publication Data
US 2013/0035383 A1    Feb. 7, 2013

(30) Foreign Application Priority Data

Jan. 29, 2010  (FR) ..................................... 10 50644
Jan. 28, 2011  (FR) ..................................... 11 50682

(51) Int. Cl.
| | | |
|---|---|---|
| C07C 51/48 | (2006.01) |
| C07D 307/00 | (2006.01) |
| B01D 11/04 | (2006.01) |
| A23L 1/30 | (2006.01) |
| C11B 1/10 | (2006.01) |
| C11C 1/02 | (2006.01) |
| C11C 3/00 | (2006.01) |

(52) U.S. Cl.
CPC ............... *B01D 11/0492* (2013.01); *A23L 1/30* (2013.01); *A23L 1/3002* (2013.01); *A23L 1/3006* (2013.01); *C11B 1/10* (2013.01); *C11C 1/025* (2013.01); *C11C 3/003* (2013.01)
USPC ........... 554/207; 554/210; 554/208; 554/209; 554/206; 549/429

(58) Field of Classification Search
USPC ........... 549/429; 554/210, 206, 208, 209, 207
See application file for complete search history.

(56) References Cited

U.S. PATENT DOCUMENTS

| | | |
|---|---|---|
| 2,530,809 A | 11/1950 | Christenson et al. |
| 4,549,990 A | 10/1985 | Seguin et al. |
| 5,403,514 A | 4/1995 | Matsuhisa et al. |
| 5,458,692 A | 10/1995 | Matsuhisa et al. |
| 6,146,616 A | 11/2000 | Msika et al. |
| 6,589,760 B1 | 7/2003 | Buchanan et al. |
| 6,673,952 B2 | 1/2004 | LeMaire et al. |
| 6,743,450 B2 | 6/2004 | Romanczyk et al. |
| 6,759,543 B2 | 7/2004 | Bardet et al. |
| 6,890,425 B2 | 5/2005 | Ackerson et al. |
| 7,161,055 B2 | 1/2007 | Choo et al. |

(Continued)

FOREIGN PATENT DOCUMENTS

| | | |
|---|---|---|
| DE | 196 08 463 | 9/1997 |
| EP | 1 246 633 A2 | 10/2002 |
| FR | 2 678 632 | 1/1993 |

(Continued)

OTHER PUBLICATIONS

Aldrich, Catalog Handbook of Fine Chemicals ( 1998-1999, p. 1161).*
International Search Report issued in application No. PCT/EP2011/051321 on Dec. 13, 2011.
"Chemicals Known or Suspected to Cause Cancer or Reproductive Toxicity," California Department of Public Health Occupational Health Branch California Safe Cosmetics Program, Nov. 1, 2012, (Sep. 1, 2009 in specification) pp. 1-36.

(Continued)

*Primary Examiner* — T. Victor Oh
(74) *Attorney, Agent, or Firm* — Foley & Lardner LLP

(57) ABSTRACT

The invention relates to a method for the extraction of all unsaponifiable fraction contained in a vegetable oil, an oil originating from a micro-organism or a vegetable butter or in a co-product from the vegetable oil refining industry, such as deodorization discharge. The method includes at least: A) a step comprising the transformation of the aforementioned oils, butter or co-product from the vegetable oil refining industry or oils originating from micro-organisms into a hydro-alcoholic solution by means of, in particular, a step selected from saponification and esterification steps; B) a step comprising the extraction of the hydro-alcoholic solution in which the fatty fraction is separated from the unsaponifiable fraction by means of liquid/liquid extraction; and C) an optional step comprising the purification of the unsaponifiable fraction, selected from the group containing crystallization and liquid/liquid extraction steps. According to the invention, at least one step from the liquid/liquid extraction steps in step B, the crystallization steps in step C and the liquid/liquid extraction steps in step C is performed using a first solvent system containing a concentration of solvent selected from among: fluorinated aromatic solvents, particularly trifluorotoluene (BTF) and hexafluorobenzene (BHF); tert-butyl ethers, particularly 2-ethoxy-2-methylpropane, also known as ethyl-tert-butyl-ether (ETBE); solvents comprising at least one silicon atom, particularly hexamethyldisiloxane (HMDS) and tetramethylsilane (TMS); methyl-tetrahydrofuran (MeTHF); and mixtures thereof, representing at least 50 vol.-% in relation to the total volume of the solvent system. The invention also relates to the fractions obtained using this method and to compositions containing said fractions.

17 Claims, No Drawings

(56) References Cited

U.S. PATENT DOCUMENTS

| | | |
|---|---|---|
| 2004/0018258 A1 | 1/2004 | Piccirilli et al. |
| 2005/0209468 A1 | 9/2005 | Burns |
| 2006/0086664 A1 | 4/2006 | Wills |
| 2006/0287533 A1 | 12/2006 | Tatsuta et al. |
| 2009/0197839 A1 | 8/2009 | Romero |

FOREIGN PATENT DOCUMENTS

| | | |
|---|---|---|
| FR | 2753200 A1 | 3/1998 |
| FR | 2762512 A1 | 10/1998 |
| FR | 2 803 598 | 7/2001 |
| GB | 2066071 * | 7/1981 |
| JP | 7-291890 | 11/1995 |

OTHER PUBLICATIONS

"CMR le Cancerogene-Mutagene-toxique pour la Reproduction (The European regulatory classification regarding carcinogenic, mutagenic and reprotoxic chemicals)," CNRS—PRC, Apr. 31, 2009, www.prc.cnrs-gif.fr/en_telechargement/cmr31.pdfn, 1 page.

"Directives—Commission Directive 2009/2/EC of Jan. 15, 2009," Official Journal of the European Union, Jan. 16, 2009, http://eur-lex.europa.eu/LexUriServ.do?url=OJ:L:2009:011:0006:0082:FR:PDF, pp. L 11/6-L 11-82.

* cited by examiner

LIQUID/LIQUID EXTRACTION

The present invention relates to a method for extracting unsaponifiable fractions, notably partial or total fractions, of vegetable oils, vegetable butters or oils from microorganisms.

The unsaponifiables or unsaponifiable fractions of a fat are the part of a fat that, after extended action of an alkaline base, remains insoluble in water and can be extracted with an organic solvent.

Most unsaponifiables of vegetable oils or butters contain several large families of substances, among which mention may be made of saturated or unsaturated hydrocarbons, aliphatic or terpene alcohols, sterols, tocopherols, carotenoid pigments, xanthophylls, as well as one or two specific and notable families of substances, in the case of certain oils and butters.

Standard methods for obtaining unsaponifiables of vegetable oils and vegetable butters aim at extracting all or part of the large families of substances contained therein for the preparation of partial or total fractions of unsaponifiables.

The partial or total fractions of unsaponifiables are sought notably for their pharmacological, cosmetic and nutritional properties.

Standard methods for obtaining unsaponifiables of vegetable oils and vegetable butters include a step comprising the saponification of the fat and extraction of the target product (the unsaponifiable) by an organic solvent.

The most commonly used solvents are solvents of oils and include alkanes (hexane, heptane, etc.) and chlorinated solvents (1,2-dichloroethane (DCE), trichloroethane, 1-chlorobutane, carbon tetrachloride, etc.). Among the latter, DCE and 1-chlorobutane are the best candidates, notably in terms of extraction yield and selectivity.

However, industrially, the toxicity of the solvent used, as well as its chemical stability, must be taken into account. For this reason, chlorinated solvents, and in particular 1,2-dichloroethane (DCE) and 1-chlorobutane, have three major disadvantages: they can break down in a basic medium (as is the case with soap solutions of saponification), they are classified among toxic solvents, notably CMR for DCE, and they have a negative impact on the environment.

Chlorinated solvents are frequently unacceptably toxic and/or dangerous.

Furthermore, from both economic and environmental points of view, methods for obtaining unsaponifiable fractions can require the use of organic solvents in quantities unsuited to the viability of the method, can include too many extraction steps and can be too slow and/or have unacceptable phase separations, for example by creating an unwanted emulsion. In particular, it can be necessary or useful to adjust the content of the fat used in the saponification process to optimize the ratio of solvent used.

The present invention thus aims to solve all or part of the problems described above. In particular, the invention aims to provide a method that is more economical, more direct, more environmentally friendly, that requires a smaller quantity of organic solvent, that is easier to implement and is faster and that generates conditions that are less toxic and/or less dangerous, improving phase separation, making it possible to obtain unsaponifiables with a yield, cost and/or selectivity at least comparable to existing methods.

In particular, it is desirable that the solvents used are less dangerous, are less toxic, are notably not classified as CMR, are more chemically stable than 1,2-dichloroethane and/or 1-chlorobutane and/or make it possible to extract unsaponifiables with a yield and/or selectivity at least comparable to the yields and selectivities obtained using 1,2-dichloroethane and/or 1-chlorobutane.

Solvents classified as CMR can be those listed in the annexes of Directive 2009/2/EC of Jan. 15, 2009, notably available at the address http://eur-lex.europa.eu/LexUriServ/LexUriServ.do?uri=OJ:L:2009:011:0006:0082:FR:PDF, referred to herein as the "EU1 CMR list", those listed in the European regulatory classification regarding carcinogenic, mutagenic and reprotoxic chemicals ($31^{st}$ ATP, 2009), notably available at the address http://www.prc.cnrs-gif.fr/en telechargement/cmr31.pdf, this second list being referred to herein as the "EU2 CMR list", and/or those listed in the document "Chemicals known or suspected to cause cancer or reproductive toxicity" dated Sep. 1, 2009 from the California Department of Public Health, Occupational Health Branch, California Safe Cosmetics Program, in the context of the California Safe Cosmetics Act of 2005, this third list being referred to herein as the "US CMR list".

In the context of the present invention, the expression "EU CMR list" refers to the EU1 CMR list and/or the EU2 CMR list.

One of the more particular objectives is to obtain a specific unsaponifiable fraction, for example having a higher content of some compounds and less of others, in particular comprising only one or certain families of compounds of the total unsaponifiable, and/or a fraction having a composition comparable to that obtained by a method involving OCE and/or 1-chlorobutane.

Unsaponifiables can be composed of numerous components, in particular comprising the large families of substances defined above and/or specific families of substances. It may be desirable to extract as completely as possible at least one of these families of substances, notably at least two, in particular at least three, particularly at least four, or at least five, particularly at least six, and even more particularly all the families of substances composing the unsaponifiable of a given oil or butter.

Said another way, the method according to the invention aims to provide a specific partial fraction of the unsaponifiable, notably with a content enriched in at least one of the families of substances composing the unsaponifiable, or to extract one or more specific compounds of the unsaponifiable, or to provide the total or near-total unsaponifiable fraction.

The present invention thus relates to a method for extracting an unsaponifiable fraction, notably a partial or total fraction, contained in a vegetable oil or butter, in an oil from a microorganism, in a concentrate of vegetable oil or butter or of oil from a microorganism, or in a by-product of the industry involving the refining of vegetable oils or oils from microorganisms, such as deodorization discharge, comprising at least:

A) a step comprising the conversion of said oils, said butter or said by-product of the industry involved in the refining of vegetable oils or oils from microorganisms to a aqueous-alcoholic solution, notably via a step selected from saponification and esterification, B) a step comprising the extraction of the aqueous-alcoholic solution in which the fat fraction is separated from the unsaponifiable fraction by liquid-liquid extraction or distillation, C) optionally, a step comprising the purification of the unsaponifiable selected from the group comprising crystallization and liquid-liquid extraction, wherein said method is characterized in that at least one step among the liquid-liquid extraction of step B, crystallization of step C and liquid-liquid extraction of step C is carried out with a first solvent system comprising a solvent content selected from fluorinated aromatic solvents, notably trifluorotoluene (BTF) and hexafluorobenzene (BHF), tert-butyl ethers, notably 2-ethoxy-2-methylpropane, also called ethyl-tert-butyl-ether (ETBE), solvents comprising at least one silicon atom, notably hexamethyldisiloxane (HMDS) and tetramethylsilane (TMS), methyl-tetrahydrofuran (MeTHF), and mixtures thereof of at least 50% by volume in relation to the total volume of the solvent system.

The CAS numbers of these various solvents are as follows:
BTF: 98-08-8;
BHF: 392-56-3;
ETBE: 37-92-3;
MTBE: 1634-04-4;
HMDS: 107-46-0;
TMS: 75-76-3; and
MeTHF: 96-47-9.

In the context of the present invention, the son "total fraction" refers to the fact that said fraction comprises all of the families of substances composing the unsaponifiable present in the given vegetable oil or in the oil coming from a microorganism or in the vegetable butter.

In the context of the present invention, the expression "partial fraction" refers to the fact that this fraction comprises at least one of the families of substances composing the unsaponifiable present in the given vegetable oil or butter or oil from a microorganism.

According to a particular embodiment, the invention relates to a method wherein step B) comprises, or consists of, liquid-liquid extraction with the first solvent system.

According to another particular embodiment, the invention relates to a method wherein step C) comprises, or consists of, crystallization or liquid-liquid extraction with the first solvent system.

According to an even more particular embodiment, the method comprises a step B) comprising or consisting of liquid-liquid extraction with a first solvent system and a step C) comprising or consisting of crystallization and/or liquid-liquid extraction with a first solvent system identical to or different from that used in step A).

Particularly, step C) can comprise purification of the unsaponifiable fraction, its enrichment in one or more families of substances composing the unsaponifiable present in the given vegetable oil, oil from a microorganism or vegetable butter. In particular, the step can further comprise isolation of a specific fraction of soya unsaponifiable, such as sterol compounds, or avocado unsaponifiable, such as furan and/or sterol compounds.

The first solvent system can comprise a solvent content selected from fluorinated aromatic solvents, notably trifluorotoluene (BTF) and hexafluorobenzene (BHF), tert-butyl ethers, notably 2-ethoxy-2-methylpropane, also called ethyl-tert-butyl-ether (ETBE), solvents comprising at least one silicon atom, notably hexamethyldisiloxane (HMDS) and tetramethylsilane (TMS), methyl-tetrahydrofuran (MeTHF), and mixtures thereof of at least 60%, notably at least 75%, in particular at least 90%, more particularly at least 95%, even more particularly at least 99% by volume in relation to the total volume of the first solvent system.

In particular, the first solvent system consists of a fluorinated aromatic solvent, notably trifluorotoluene (BTF) and hexafluorobenzene (BHF), tert-butyl ether, notably 2-ethoxy-2-methylpropane, also called ethyl-tert-butyl-ether (ETBE), solvent comprising at least one silicon atom, notably hexamethyldisiloxane (HMDS) and tetramethylsilane (TMS), methyl-tetrahydrofuran (MeTHF), or a mixture thereof.

The first solvent system can comprise a content in a solvent selected from fluorinated aromatic solvents, notably trifluorotoluene (BTF) and hexafluorobenzene (BHF), tert-butyl ethers, notably 2-ethoxy-2-methylpropane, also called ethyl-tert-butyl-ether (ETBE), solvents comprising at least one silicon atom, notably hexamethyldisiloxane (HMDS) and tetramethylsilane (TMS), and methyl-tetrahydrofuran (MeTHF) of at least 50%, notably at least 75%, in particular at least 90%, more particularly at least 95%, even more particularly at least 99% by volume in relation to the total volume of the first solvent system.

According to one variant, the first solvent system consists of a fluorinated aromatic solvent, notably trifluorotoluene (BTF) and hexafluorobenzene (BHF), a tert-butyl ether, notably 2-ethoxy-2-methylpropane, also called ethyl-tert-butyl-ether (ETBE), a solvent comprising at Least one silicon atom, notably hexamethyldisiloxane (HMDS), tetramethylsilane (TMS) or methyl-tetrahydrofuran (MeTHF).

According to a second variant, the first solvent system consists of a first solvent selected from fluorinated aromatic solvents, notably trifluorotoluene (BTF) and hexafluorobenzene (BHF), tert-butyl ethers, notably 2-ethoxy-2-methylpropane, also called ethyl-tert-butyl-ether (ETBE), solvents comprising at least one silicon atom, notably hexamethyldisiloxane (HMDS) and tetramethylsilane (TMS), methyl-tetrahydrofuran (MeTHF), and a second solvent, not identical to the first, selected from fluorinated aromatic solvents, notably trifluorotoluene (BTF) and hexafluorobenzene (BHF), tert-butyl ethers, notably 2-ethoxy-2-methylpropane, also called ethyl-tert-butyl-ether (ETBE), and 2-methoxy-2-methylpropane, also called methyl tert-butyl ether (MTBE), solvents comprising at least one silicon atom, notably hexamethyldisiloxane (HMDS) and tetramethylsilane (TMS), methyl-tetrahydrofuran (MeTHF).

According to a third variant, the first solvent system consists of one or more solvents selected from HMDS, HFB and BTF and one or more solvents selected from MeTHF, MTBE, ETBE and TMS.

According to a fourth variant, the first solvent system consists of HMDS and MeTHF, in particular in proportions ranging from 50/50 to 90/10 (volume/volume).

Furthermore, the proportion of HMDS used in the first solvent system can play an important part in the consumption of solvents or washing water and/or in extraction time. It can also facilitate decanting and thus cause the formation of lower-quality emulsions and/or faster phase separation during extraction and/or washing steps.

According to a fifth variant, the first solvent system consists of ETBE.

According to a particular embodiment, the first solvent system has a CMR solvent content, in particular solvents on the EU1, EU2, and/or US CMR lists, less than or equal to 10%, notably less than or equal to 5%, in particular less than or equal to 2%, particularly less than or equal to 1%, even more particularly less than or equal to 0.5%, even less than or equal to 0.1% by volume in relation to the total volume of the first solvent system.

Still more particularly, the first solvent system is free of solvents present on the EU1, EU2 and/or US CMR lists.

The solvents used in the first solvent system have a purity of at least 90%, notably at least 95%, in particular at least 98%, particularly at least 99%, even at least 99.5%.

In particular, step A) comprising the conversion of oil, butter or by-product of the vegetable oil refining industry in a aqueous-alcoholic solution, notably via a step selected from saponification and esterification, is carried out in a second solvent system comprising a content of solvents selected from $C_2$-$C_4$ alcohols, and notably ethanol, n-propanol, isopropanol, butanol, in particular n-butanol, MeTHF and mixtures thereof of at least 50% by volume in relation to the total volume of the second solvent system.

The second solvent system can comprise a content in a solvent selected from $C_2$-$C_4$ alcohols, and notably ethanol, n-propanol, isopropanol, butanol, in particular n-butanol, MeTHF and mixtures thereof of at least 60%, notably at least 75%, in particular at least 90%, more particularly at least 95%, even more particularly at least 99% by volume in relation to the total volume of the second solvent system.

In particular, the second solvent system consists of ethanol, n-propanol, isopropanol, butanol, MeTHF or a mixture thereof.

The second solvent system can comprise a content in a solvent selected from C2-$C_4$ alcohols, and notably ethanol, n-propanol, isopropanol, butanol, in particular n-butanol, and MeTHF, of at least 50%, notably at least 75%, in particular at least 90%, more particularly at least 95%, even more particularly at least 99% by volume in relation to the total volume of the second solvent system.

According to a particular embodiment, the second solvent system comprises a content in a solvent present on the EU1, EU2 and/or US CMR lists less than or equal to 10%, notably less than or equal to 5%, in particular less than or equal to 2%, particularly less than or equal to 1%, even more particularly less than or equal to 0.5%, even less than or equal to 0.1% by volume in relation to the total volume of the second solvent system.

Still more particularly, the second solvent system is free of solvents present on the EU1, EU2 and/or US CMR lists.

The solvents used in the second solvent system have a purity of at least 90%, notably at least 95%, in particular at least 98%, particularly at least 99%, even at least 99.5%.

In the context of the present invention, the expression "diluted aqueous-alcoholic solution" (or "DAS") refers to diluted saponification reaction medium notably comprising water and one or more very polar solvents selected in particular from alcohols, for example $C_2$-$C_4$ alcohols, and MeTHF.

The diluted aqueous-alcoholic solution (DAS) extracted can have a water content greater than or equal to 50%, notably greater than or equal to 60%, in particular greater than or equal to 65%, particularly greater than or equal to 70%, even greater than or equal to 72% by volume in relation to the volume of the aqueous-alcoholic solution.

The diluted aqueous-alcoholic solution (DAS) to be extracted can have a water content less than or equal to 95%, notably less than or equal to 90%, in particular less than or equal to 85%, particularly less than or equal to 80%, even less than or equal to 75% by volume in relation to the volume of the aqueous-alcoholic solution.

The ratio (volume/volume) of DAS to be extracted to the solvent system can range from 0.1 to 10, notably from 0.25 to 5, in particular from 0.5 to 2.

The method according to the invention provides an unsaponifiable fraction that is virtually identical to the unsaponifiable fraction obtained by a "classic" method as described in Example 1 below using 1,2-dichloroethane or 1-chlorobutane.

In the context of the present invention, the expression "virtually identical unsaponifiable fraction" refers to an unsaponifiable fraction that has a chromatographic profile and/or a composition similar to a reference fraction obtained by extraction in DCE or 1-chlorobutane, notably classic extraction in DCE or 1-chlorobutane.

In the context of the present invention, the expression "chromatographic profile similar to" refers to a chromatographic profile characterized in that said chromatographic profile comprises all of the families of unsaponifiable observed in the reference fraction obtained by a classic method according to extraction in 1,2-dichloroethane or 1-chlorobutane.

In the context of the present invention, the expression "composition similar to" refers to a composition characterized in that the content of compounds of the various families of the unsaponifiable extract is of the same order of magnitude as that observed in the reference fraction obtained by a classic method according to extraction in 1,2-dichloroethane or 1-chlorobutane, and more particularly corresponding to the following content in relation to the reference fraction (% by mass in relation to the mass of the reference fraction):

| Avocado | |
|---|---|
| Furan compounds | ±15% |
| Trihydroxyl alcohols | ±2% |
| Hydrocarbons | ±0.5% |
| Squalene | ±0.5% |
| Sterols | ±1.5% |
| Unidentified | ±5% |
| Soya | |
| Hydrocarbons | ±0.5% |
| Squalene | ±2% |
| Tocopherols | ±8% |
| Sterols | ±10% |
| Unidentified | ±3% |

In the present case, "±Y %" means that, if the reference value is X %, the contents can range from (X−Y) % to (X+Y) %. If X is 70% and Y is 15%, the content can range from 55% to 85%.

To be specific, the "unidentified" part cannot be within in the range specified above.

In the context of the present invention, the expression "classic extraction in 1,2-dichloroethane or 1-chlorobutane" refers to extraction in 1,2 dichloroethane or 1-chlorobutane according to the method defined in Example 1, starting with the same raw material as that used during extraction of an unsaponifiable with another solvent system.

In the context of the present invention, the expression "reference fraction" refers to an unsaponifiable extracted in 1,2 dichloroethane or 1-chlorobutane, starting with the same raw material as that used during extraction of an unsaponifiable with another solvent system.

For example, in the case of avocado and soya according to the protocols described in Example 1 in patent EP 1,246,633 B1.

The present invention further relates to a method for extracting an unsaponifiable fraction, notably a partial or total fraction, contained in a vegetable oil, an oil from a microorganism, a vegetable butter or a by-product of the industry involved in the refining of vegetable oils, notably avocado and/or soya oils, or oils from microorganisms comprising at least:

A) a saponification step wherein said oils, said butter or said by-product of the industry involved in the refining of vegetable oils or oils from microorganisms is transformed into a aqueous-alcoholic solution, B) a step comprising the extraction of the aqueous-alcoholic solution by a first solvent system as defined above.

More particularly, the method for extracting the unsaponifiable fraction of a soya oil of the present invention is such that a liquid-liquid extraction is carried out by bringing together DAS with a first DAS solvent system, notably using counter-current extraction, by means of a first solvent system as defined above, in particular comprised of BTF, wherein the ratio (volume/volume) of solvent system to DAS ranges from 0.1 to 10, notably from 0.25 to 5, in particular from 0.5 to 2.

More particularly, the inventive method for extracting the unsaponifiable fraction of an avocado oil is such that liquid-liquid extraction is carried out by bringing together DAS with a first DAS solvent system, notably using counter-current extraction, by means of a solvent system, in particular comprised of a mixture of ETBE, wherein the ratio (volume/volume) of solvent system to DAS ranges from 0.1 to 10, notably from 0.25 to 5, in particular from 0.5 to 2.

The vegetable oil or oil from a microorganism used in the present method can be selected from oil of soya, quinoa, rapeseed, corn, sunflower, sesame, lupin, cotton, coconut, olive, palm leaf, wheat germ, alfalfa, avocado, palm kernel, groundnut, copra, flax, castor bean, grape seeds, squash seeds, blackcurrant seeds, melon seeds, tomato seeds, pumpkin seeds, almond, hazelnut, nut, evening primrose, borage, safflower, false flax, oil poppy, macroalgae, microalgae such as *Chlorella*, and/or microorganisms, notably salt water, fresh water or ground water microorganisms, in particular yeasts, molds and, more particularly, bacteria, and mixtures thereof.

The vegetable butter can be selected from cocoa butter, illipe butter, shea butter, and mixtures thereof.

Comparison of the unsaponifiable contents of the various vegetable oils—soya, cotton, coconut, olive and avocado—show that the avocado oil obtained by extraction according to various known methods has a particularly high level of unsaponifiable.

Typically, the contents of unsaponifiable fraction obtained range from 2% to 10% in avocado oil, are roughly 0.5% in coconut oil, roughly 1% in soya oil and roughly 1% in olive oil.

The avocado unsaponifiable can be prepared by extraction from avocado oil.

The method for extracting avocado oil unsaponifiable can be carried out as follows.

According to a method known to the person skilled in the art, either:
  fresh pulp is pressed in the presence of a third water-absorbing fibrous body, such as coffee hull, in a cage press, and then the oil and water emulsion obtained is separated by decantation and/or centrifugation; or
  fresh pulp is ground and brought together with a suitable organic solvent (a methanol-chloroform mixture, for example), and then the oil is recovered by evaporation of the solvent. Several methods for extracting the unsaponifiable fraction from a vegetable oil have been described in the prior art.

Notable mention may be made of the method for preparing avocado oil unsaponifiable as described and claimed in patent FR 2,678,632 in the name of Laboratoires Pharmascience. Said method provides a furan-rich fraction (fraction H) of avocado unsaponifiable, in relation to classic methods for preparing avocado unsaponifiable.

Thus, the avocado oil unsaponifiable used according to the invention can be obtained from fresh fruit but, preferably, the avocado unsaponifiable is prepared from fruit heat-treated beforehand, before oil extraction and saponification, as described in patent FR 2,678,632.

Said heat treatment consists of controlled drying of the fruit, preferably fresh, for at least four hours, advantageously at least 10 hours, preferably between roughly 24 and roughly 48 hours, at a temperature preferably of at least roughly 80° C. and preferably between roughly 80 and roughly 120° C.

Mention may also be made of the method for preparing soya oil unsaponifiable, obtained from a soya oil unsaponifiable concentrate.

Said unsaponifiable concentrate is prepared by molecular distillation according to a method as described for lupin oil in patent application FR 2,762,512, but adapted to soya oil.

In said method, the soya oil is distilled in a centrifugal or wiped-film molecular distiller at a temperature between roughly 210 and 250° C. and under high vacuum, ranging between 0.01 and 0.001 mmHg (0.13 to 1.3 Pa).

The distillate obtained has an unsaponifiable content between 5% and 40% by volume and thus constitutes a soya oil unsaponifiable concentrate.

The concentrate is then saponified with a base such as potash or soda in polar medium, notably alcoholic medium, preferably of ethanol, n-propanol, isopropanol, butanol, in particular n-butanol, MeTHF, or a mixture thereof, and then it undergoes one or more extractions with the first solvent system.

The extraction solution obtained is preferably then centrifuged, filtered and then washed with water to eliminate residual traces of alkalinity.

The extraction solvent is evaporated carefully to recover the unsaponifiable.

Finally, before it is saponified, the oil can be enriched in unsaponifiable by separating a majority of the components of the unsaponifiable, which are recovered in a concentrate. Various methods can be used, including cold crystallization, liquid-liquid extraction and molecular distillation.

The preliminary unsaponifiable concentration of the oil makes it possible to decrease the volumes of oil to be saponified.

Molecular distillation is particularly preferred, being carried out preferably at a temperature between roughly 180 and roughly 230° C. while maintaining pressure between $10^{-3}$ and $10^{-2}$ mmHg, preferably on the order of $10^{-3}$ mmHg.

The unsaponifiable concentration of the distillate can reach 60% by mass in relation to the total mass.

Particularly, the present invention relates to a method as described above wherein the unsaponifiable obtained is selected from a soya unsaponifiable, an avocado unsaponifiable, notably a furan fraction-rich avocado unsaponifiable and/or a sterol fraction-rich avocado unsaponifiable, and even more particularly a mixture of avocado and soya unsaponifiables (ASU).

The method according to the present invention makes it possible to extract an unsaponifiable fraction contained in a vegetable oil, an oil from a microorganism or a vegetable butter. It can also make it possible to extract an unsaponifiable fraction from a by-product of the industry involved in the refining of vegetable oils or oils from a microorganism, such as deodorization discharge, for example, also called deodistillates, produced during the refining of vegetable oils or oils from microorganisms.

The fatty acids and partial glycerides present in the deodistillates may indeed be saponified or esterified with a light alcohol, with an aim of separating the fat fraction from the unsaponifiable fraction, either by liquid-liquid extraction or by vacuum distillation.

Finally, purification at the unsaponifiable or the separated active fractions, most often tocopherols (including vitamin E) and sterols, notably involves steps of crystallization in an organic solvent or liquid-liquid extraction.

The present invention also relates to a method for extracting the unsaponifiable fraction in a by-product of the industry involved in the refining of vegetable oils or oils from a microorganism, wherein said by-product is a deodistillate of a vegetable oil or an oil from a microorganism, said method comprising at least:

- a step comprising the saponification in which the deodistillate is converted into an aqueous-alcoholic solution,
- a step comprising the counter-current extraction of the aqueous-alcoholic solution by means of the first solvent system,
- a step comprising the crystallization of sterols and/or triterpene alcohols,
- a step comprising the separation of an active compound, such as tocopherols, tocotrienols, squalene and carotenes, wherein said separation step is selected from the group comprised of extractions, in particular by means of the first solvent system, and distillations.

Particularly, the crystallization of sterols and/or triterpene alcohols can be carried out in the first solvent system.

The present invention further relates to an unsaponifiable fraction, notably a partial or total fraction, free of solvents classified in the EU1, EU2 and/or US CMR lists, wherein in particular said fraction is obtained by the extraction method according to the present invention.

The present invention further relates to the use of said fraction for preparing a composition, notably a pharmaceutical, dietary and/or cosmetic composition, or a dietary supplement.

The present invention further relates to a composition, notably a dietary, cosmetic or pharmaceutical composition, or a dietary supplement, comprising at least one unsaponifiable fraction of at least one vegetable oil or oil from a microorganism, said fraction being free of solvents classified in the EU1, EU2 and/or US CMR lists and/or said fraction being able to be obtained, or directly obtained, by the method according to the invention, and said composition optionally comprising an excipient, in particular a cosmetically, dietary or pharmaceutically acceptable excipient.

According to a particular embodiment, the present invention relates to a composition, notably a pharmaceutical, dietary or cosmetic composition, or a dietary supplement, comprising at least one unsaponifiable, in particular a soya unsaponifiable, an avocado unsaponifiable, particularly a furan fraction-rich avocado unsaponifiable and/or a sterol fraction-rich avocado unsaponifiable, and even more particularly a mixture of avocado and soya unsaponifiables (ASU) able to be obtained or directly obtained by the method according to the invention.

The pharmaceutical compositions can be intended to prevent and/or treat disorders of the conjunctive tissue, notably osteoarthritis, periodontopathy and/or aging of the skin.

The dietary compositions or dietary supplements can be intended to prevent and/or treat disorders of the conjunctive tissue, notably osteoarthritis, periodontopathy and aging and/or inflammation of the skin.

The cosmetic compositions can be intended to prevent and/or treat skin disorders of the epidermis, dermis and/or hypodermis.

In the context of the present invention, the expression "free of solvents classified in the EU1, EU2 and/or US CMR lists" refers to a total content in solvents classified in the EU1, EU2 and/or US CMR lists less than 10 ppm, notably less than 5 ppm, in particular less than 2 ppm, even less than 1 ppm.

The present invention further relates to a cosmetic treatment method wherein the cosmetic composition of the invention is applied topically and also to the use of an unsaponifiable of a vegetable oil, an oil from a microorganism or a vegetable butter obtained according to the present invention for the manufacture of a drug, in particular a drug intended to treat or prevent disorders of the conjunctive tissue, and notably osteoarthritis.

Of course, the various characteristics described in the present description can be combined.

The following experiments were performed as examples illustrating the present invention.

EXAMPLES

Example 1

Extraction of Avocado Unsaponifiable with DCE (Reference 1)

The first step consists in saponifying a concentrate prepared by molecular distillation of avocado oil.

To this end, into a 100 ml round-bottom flask equipped with a refrigerant are successively added a given mass of avocado oil concentrate (45.6 g) and then ethanol (36.6 g), 50% potash (5.2 g) and several grains of pumice.

The system is then refluxed for 3.5 hours and then, after cooling, diluted with demineralized water (60 ml).

After saponification, an aqueous-alcoholic solution is obtained containing the unsaponifiable (or unsaponifiable fraction) in solution. This unsaponifiable is then extracted with a first solvent system, to be specific DCE.

Several successive extractions (5×70 ml) are carried out; the organic phases thus collected are then combined and washed with tap water (5×70 ml) to neutrality (phenolphthalein test).

The solvent phase obtained is then dried on anhydrous sodium sulfate and then filtered; the unsaponifiable is then recovered by evaporation of the solvent in a rotary evaporator. The unsaponifiable thus extracted is weighed and stored in a pill-making machine under inert atmosphere.

The composition of the extracted unsaponifiable is then measured by gas-phase chromatography (GPC). The results are presented in Table 1 below.

Example 2

Extraction of Avocado Unsaponifiable with HMDS

The extraction is carried out according to the procedure of Example 1 which, after optimization to adapt it to the new solvent system, consists of an extraction step with 4×70 ml of HMDS instead DCE and a step comprising the washing of the organic phases with 3×70 ml of water. Measurements are taken as in Example 1 and the results are presented in Table 1 below.

Example 3

Extraction of Avocado Unsaponifiable with a HMDS-MeTHF Mixture (90/10 by Volume)

The extraction is carried out according to the procedure of Example 1 which, after optimization to adapt it to the new solvent system, consists of an extraction step with 4×70 ml of a HMDS-MeTHF mixture (90/10 by volume) instead of DCE and a step comprising the washing of the organic phases with 2×70 ml of water. Measurements are taken as in Example 1 and the results are presented in Table 1 below.

Example 4

Extraction of Avocado Unsaponifiable with a HMDS-MeTHF Mixture (50/50 by Volume)

The extraction is carried out according to the procedure of Example 1 which, after optimization to adapt it to the new solvent system, consists of an extraction step with 6×70 ml of a HMDS-MeTHF mixture (50/50 by volume) instead of DOE and a step comprising the washing of the organic phases with 8×70 ml of water. Measurements are taken as in Example 1 and the results are presented in Table 1 below.

TABLE 1

Analysis: chromatographic profile and composition of the extracted unsaponifiable of Examples 1 to 4

| | | Ex. 1 | Ex. 2 | Ex. 3 | Ex. 4 |
|---|---|---|---|---|---|
| Specific compounds | Furan compounds | 63.7 | 80.3 | 77.6 | 52.4 |
| | Trihydroxyl alcohols | 8.6 | 0.4 | 1 | 14.0 |
| Hydrocarbons | | 1.2 | 1.4 | 1.4 | 1.1 |
| Squalene | | 1.1 | 1.4 | 1.3 | 1.0 |
| Tocopherols | | Traces | Traces | Traces | Traces |
| Sterols | | 3.5 | 1.2 | 2.4 | 3.4 |
| Others | | 11.6 | 12.3 | 10.0 | 9.7 |
| Mass yield in relation to the concentrate | | 39% | 28% | 29% | 45% |

Mass yield in relation to the concentrate = 100 × (mass of extracted unsaponifiable/mass of concentrate used).

The mixtures tested resulted in extraction of the unsaponifiable. All the unsaponifiables obtained have a chromatographic profile similar to that observed with the reference product extracted with DCE.

However, their composition demonstrates the influence of the polarity characteristics of the first solvent system on selectivity potential in terms of the components of the extracted unsaponifiable. With the most polar mixture, the most polar compounds are extracted in greater proportions.

HMDS used alone enables selective extraction of non-polar compounds.

Thus, a HMDS/MeTHF mixture makes it possible to extract an unsaponifiable with a chromatographic profile similar to that of the reference unsaponifiable. The composition of the extracted unsaponifiable is directly related to the composition of the solvent system and more particularly to its polarity: the more polar the solvent system, the richer the unsaponifiable in polar compounds such as trihydroxyl alcohols. Conversely, the more non-polar the solvent system, the more selective the extraction and the unsaponifiable rich in non-polar compounds such as furan compounds.

Moreover, the composition of the first solvent system, due to its weak polarity, makes it possible to improve the extraction and washing steps by limiting the quantities of solvents and/or water used as well as facilitating phase separation.

Example 5

Extraction of Avocado Unsaponifiable with ETBE

The extraction is carried out according to the procedure of Example 1 which, after optimization to adapt it to the new solvent system, consists of an extraction step with 4×60 ml of ETBE instead of DCE and a step comprising the washing of the organic phases with 4×70 ml of water. Measurements are taken as in Example 1 and the results are presented in Table 2 below.

TABLE 2

Analysis: chromatographic profile and composition of the extracted unsaponifiable of Examples 1 and 5.

| | | Ex. 1 | Ex. 5 |
|---|---|---|---|
| Specific compounds | Furan compounds | 63.7 | 63.8 |
| | Trihydroxyl alcohols | 8.6 | 7.1 |
| Hydrocarbons | | 1.2 | 1.2 |
| Squalene | | 1.1 | 1.1 |
| Tocopherols | | Traces | Traces |
| Sterols | | 3.5 | 3.0 |
| Others | | 11.6 | 11.4 |
| Mass yield in relation to the concentrate | | 39% | 36% |

The first solvent system tested results in extraction of the unsaponifiable with a mass yield similar to that obtained during classic extraction with DCE. The unsaponifiable obtained has a chromatographic profile and a composition similar to those observed with the reference product extracted with DCE.

Moreover, ETBE makes it possible to decrease the number of extractions and thus the quantity of solvents as well as the number of washings and thus the quantity of water to be implemented to extract the unsaponifiable fraction of an avocado concentrate.

In conclusion, ETBE is a good alternative to the use of DCE as a first solvent system in the method for extracting avocado unsaponifiable.

Example 6

Extraction of Avocado Unsaponifiable with 1-chlorobutane (Reference 2)

Extraction and washing are carried out according to the procedure of Example 1 with 1-chlorobutane instead of DCE. Measurements are taken as in Example 1 and the results are presented in Table 3 below.

Example 7

Extraction of Avocado Unsaponifiable with BTF

Saponification is carried out according to the procedure of Example 1 with ethanol replaced by isopropanol (36.6 ml). The extraction is carried out according to the procedure of Example 1 which, after optimization to adapt it to the new solvent system, consists of an extraction step with 4×35 ml of BTF instead of DCE and a step comprising the washing of the organic phases with 4×35 ml of water. Measurements are taken as in Example 1 and the results are presented in Table 1 below.

Example 8

Extraction of Avocado Unsaponifiable with HMDS

Saponification is carried out according to the procedure of Example 1 with ethanol replaced by MeTHF (36.6 ml). The extraction is carried out according to the procedure of Example 1 which, after optimization to adapt it to the new solvent system, consists of an extraction step with 3×70 ml of HMDS instead of DCE and a step comprising the washing of the organic phases with 3×70 ml of water. Measurements are taken as in Example 1 and the results are presented in Table 3 below.

TABLE 3

Analysis: chromatographic profile and composition of the extracted unsaponifiable of Examples 6 to 8.

|  |  | Ex. 6 | Ex. 7 | Ex. 8 |
|---|---|---|---|---|
| Specific compounds | Furan compounds | 60.7 | 72.5 | 70.0 |
|  | Trihydroxyl alcohols | 5.5 | 3.1 | 2.8 |
| Hydrocarbons |  | 1.1 | 1.4 | 1.2 |
| Squalene |  | 1.1 | 1.3 | 1.2 |
| Tocopherols |  | Traces | Traces | Traces |
| Sterols |  | 3.1 | 3.1 | 2.4 |
| Others |  | 14.0 | 9.8 | 14.8 |

The use of MeTHF in the second solvent system coupled with that of HMDS in the first solvent system results in extraction of the unsaponifiable. The unsaponifiable obtained has a chromatographic profile and a composition similar to those observed with the reference product extracted with 1-chlorobutane.

Similarly, the use of the isopropanol in the second solvent system coupled with that of BTF in the first solvent system results in extraction of the unsaponifiable. The unsaponifiable obtained has a chromatographic profile and a composition similar to those observed with the reference product extracted with 1-chlorobutane.

The use of MeTHF in the second solvent system coupled with that of HMDS in the first solvent system and isopropanol in the second solvent system coupled with that of BTF in the first solvent system decreases the number of extractions and the quantities of solvents used as well as the number of washings and the quantities of water to be used.

In conclusion, the combination of MeTHF/HMDS and isopropanol/BTF is shown to be a good alternative to the use of ethanol/1-chlorobutane by enabling the extraction of unsaponifiables with profiles and compositions similar to the reference product while decreasing the quantities of solvents and water used.

Example 9

Extraction of Soya Unsaponifiable with DCE

The first step consists of saponifying a soya concentrate. To this end, into a 100 ml round-bottom flask equipped with a refrigerant are successively added a given mass of soya oil concentrate (10.0 g) and then ethanol (23.3 ml), 50% potash (1.7 ml) and several grains of pumice.

The system is then refluxed for 3 hours and then diluted with demineralized water (60 ml).

After saponification, an aqueous-alcoholic solution is obtained containing the unsaponifiable (or unsaponifiable fraction) in solution. This unsaponifiable is then extracted with a first solvent system, to be specific DCE.

Several successive extractions (5×43 ml) are carried out; the organic phases thus collected are then combined and washed with water (7×43 ml) to neutrality (phenolphthalein test).

The solvent phase obtained is then dried on anhydrous sodium sulfate and then filtered; the unsaponifiable is then recovered by evaporation of the solvent in a rotary evaporator. The unsaponifiable thus extracted is weighed and stored in a pill-making machine under inert atmosphere.

The composition of the extracted unsaponifiable is then measured by gas-phase chromatography (GPC). The results are presented in Table 4 below.

Example 10

Extraction of Soya Unsaponifiable with BTF

Saponification is carried out according to the procedure of Example 9 with the volume of ethanol increased (50.0 ml). The extraction is carried out according to the procedure of Example 9 which, after optimization to adapt it to the new solvent system, consists of an extraction step with 7×35 ml of BTF instead of DCE and a step comprising the washing of the organic phases with 10×35 ml of water. Measurements are taken as in Example 9 and the results are presented in Table 4 below.

Example 11

Extraction of Soya Unsaponifiable with a HMDS-MeTHF Mixture (50/50 by Volume)

The extraction is carried out according to the procedure of Example 9 which, after optimization to adapt it to the new solvent system, consists of an extraction step with 5×43 ml of a HMDS-MeTHF mixture (50/50 by volume) instead of DCE and a step comprising the washing of the organic phases with 4×43 ml of water. Measurements are taken as in Example 9 and the results are presented in Table 4 below.

TABLE 4

Analysis: chromatographic profile and composition of the extracted unsaponifiable of Examples 9 to 11

|  | Ex. 9 | Ex. 10 | Ex. 11 |
|---|---|---|---|
| Hydrocarbons | 0.1 | 0.2 | 0.1 |
| Squalene | 4.4 | 4.5 | 3.9 |
| Tocopherols | 25.8 | 23.4 | 19.8 |
| Sterols | 44.3 | 43.7 | 41.0 |
| Others | 6.0 | 6.1 | 4.6 |
| Mass yield in relation to the concentrate | 45% | 38% | 49% |

The first solvent systems tested result in extraction of the unsaponifiable. The unsaponifiable obtained has a chromatographic profile and a composition similar to those observed with the reference product extracted with DCE.

In conclusion, BTF and a 50% by volume HMDS/MeTHF mixture appear to be good alternatives to the use of DCE.

Example 12

Extraction of Rapeseed Unsaponifiable with BTF

Saponification is carried out according to the procedure of Example 10 with the concentrate being rapeseed concentrate. Extraction is carried out according to the procedure of Example 10. Measurements are taken as in Example 10 and the results are presented in Table 5 below.

Example 13

Extraction of Corn Unsaponifiable with BTF

Saponification is carried out according to the procedure of Example 10 with the concentrate being corn concentrate. The extraction is carried out according to the procedure of Example 10. Measurements are taken as in Example 10 and the results are presented in Table 5 below.

Example 14

Extraction of Sunflower Unsaponifiable with BTF

Saponification is carried out according to the procedure of Example 10 with the concentrate being sunflower concentrate. The extraction is carried out according to the procedure of Example 10. Measurements are taken as in Example 10 and the results are presented in Table 5 below.

TABLE 5

Analysis: chromatographic profile and composition of the extracted unsaponifiable of Examples 10 and 12 to 14.

|  | Ex. 10 | Ex. 12 | Ex. 13 | Ex. 14 |
|---|---|---|---|---|
| Tocopherols (%) | 23.4 | 6.4 | 7.9 | 9.7 |
| Sterols (%) | 43.7 | 63.1 | 55.3 | 58.7 |
| Mass yield in relation to the concentrate | 38% | 7.2% | 9.0% | 4.0% |
| Mass yield in relation to the unsaponifiable | 79% | 76% | 83% | 78% |

BTF applied to various vegetable matter gives equivalent results in terms of mass yield in relation to the unsaponifiable.

Example 15

Extraction of Sesame Unsaponifiable with ETBE

Saponification is carried out according to the procedure of Example 5 with the concentrate being sesame concentrate. Extraction is carried out according to the procedure of Example 5. Measurements are taken as in Example 5 and the results are presented in Table 6 below.

Example 16

Extraction of Sesame Unsaponifiable with a HMDS-MeTHF Mixture (50/50 by Volume)

Saponification is carried out according to the procedure of Example 4 with the concentrate being sesame concentrate. Extraction is carried out according to the procedure of Example 4. Measurements are taken as in Example 4 and the results are presented in
Table 6 below.

TABLE 6

Analysis: chromatographic profile and composition of the extracted unsaponifiable of Examples 15 and 16

|  | Ex. 15 | Ex. 16 |
|---|---|---|
| Sterols (%) | 17.4 | 20.0 |
| Sesamin (%) | 28.0 | 31.4 |
| Sesamolin (%) | 13.3 | 15.7 |
| Mass yield in relation to the concentrate | 12% | 15% |
| Mass yield in relation to the unsaponifiable | 83% | 98% |

Both ETBE and the HMDS-MeTHF mixture (50/50 by volume) are good extraction solvents for sesame unsaponifiable. The HMDS-MeTHF mixture has excellent extractive capacity with an unsaponifiable extraction yield of 98% by mass.

Example 17

Extraction of Palm Unsaponifiable with BTF

Saponification is carried out according to the procedure of Example 10 with the concentrate being palm concentrate. Extraction is carried out according to the procedure of Example 10. Measurements are taken as in Example 10 and the results are presented in Table 7 below.

Example 18

Extraction of Palm Unsaponifiable with a HMDS-MeTHF Mixture (50/50 by Volume)

Saponification is carried out according to the procedure of Example 11 with the concentrate being palm concentrate. Extraction is carried out according to the procedure of Example 11. Measurements are taken as in Example 11 and the results are presented in Table 7 below.

TABLE 7

Analysis: chromatographic profile and composition of the extracted unsaponifiable of Examples 17 and 18

|  | Ex. 17 | Ex. 18 |
|---|---|---|
| Sterols (%) | 23.0 | 25.0 |
| Tocopherols (%) | 3.7 | 3.2 |
| Tocotrienols (%) | 11.4 | 8.9 |
| Carotenes | 0.6 | 0.5 |
| Mass yield in relation to the concentrate | 2% | 3% |
| Mass yield in relation to the unsaponifiable | 75% | 99% |

Both BTF and the HMDS-MeTHF mixture (50/50 by volume) are good extraction solvents for palm unsaponifiable. The HMDS-MeTHF mixture has excellent extractive capacity with an unsaponifiable extraction yield of 99% by mass.

The invention claimed is:

1. A method for extracting an unsaponifiable fraction contained in a vegetable oil, an oil from a microorganism or a vegetable butter, or in a by-product of the industry involved in the refining of vegetable oils or oils from microorganisms, comprising at least:

A) converting said oils, said butter or said by-product of the industry involved in the refining of vegetable oils or oils from microorganisms to a aqueous-alcoholic solution, by a step selected from saponification and esterification, B) extracting the aqueous-alcoholic solution in which the fat fraction is separated from the unsaponifiable fraction by liquid-liquid extraction, C) optionally, purifying the unsaponifiable selected from the group comprising crystallization and liquid-liquid extraction, wherein at least one step among the liquid-liquid extraction of step B, crystallization of step C and liquid-liquid extraction of step C is carried out with a first solvent system comprising a solvent content selected from fluorinated aromatic solvents, tert-butyl ethers, solvents comprising at least one silicon atom, methyl-tetrahydrofuran (MeTHF), and mixtures thereof of at least 50% by volume in relation to the total volume of the solvent system.

2. A method according to claim 1, wherein step B) comprises liquid-liquid extraction with the first solvent system.

3. A method according to claim 1, wherein step C) comprises crystallization and/or liquid-liquid extraction with the first solvent system.

4. A method according to claim 1, wherein the first solvent system comprises a solvent content selected from fluorinated aromatic solvents, tert-butyl ethers, solvents comprising at least one silicon atom, methyl-tetrahydrofuran (MeTHF), and mixtures thereof, of at least 75%, by volume in relation to the total volume of the first solvent system.

5. A method according to claim 1, wherein the first solvent system consists of a fluorinated aromatic solvent, tert-butyl ether, solvent comprising at least one silicon atom, methyl-tetrahydrofuran (MeTHF), or a mixture thereof.

6. A method according to claim 1, wherein the first solvent system comprises a solvent content selected from fluorinated aromatic solvents, tert-butyl ethers, solvents comprising at least one silicon atom, methyl-tetrahydrofuran (MeTHF), and mixtures thereof of at least 90%, by volume in relation to the total volume of the first solvent system.

7. A method according to claim 1, wherein step A) comprising the conversion of the oil or butter to an aqueous-alcoholic solution, via a step selected from saponification and esterification, is carried out in a second solvent system comprising a content of solvents selected from C2-C4 alcohols, methyl-tetrahydrofuran (MeTHF) and mixtures thereof of at least 50% by volume in relation to the total volume of the solvent system.

8. A method according to claim 7, wherein the second solvent system comprises a content in a solvent selected from C2-C4 alcohols, methyl-tetrahydrofuran (MeTHF) and mixtures thereof of at least 60%, by volume in relation to the total volume of the second solvent system.

9. A method according to claim 7, wherein the second solvent system comprises C2-C4 alcohols, MeTHF, or a mixture thereof.

10. A method according to 7, wherein the second solvent system comprises a content in a solvent selected from C2-C4 alcohols, methyl-tetrahydrofuran (MeTHF), of at least 75%, by volume in relation to the total volume of the second solvent system.

11. A method according to claim 1, wherein the vegetable oil, oil from a microorganism or vegetable butter is selected from oil of soya, quinoa, rapeseed, corn, sunflower, sesame, lupin, cotton, coconut, olive, palm leaf, wheat germ, alfalfa, avocado, palm kernel, groundnut, copra, flax, castor bean, grape seeds, squash seeds, blackcurrant seeds, melon seeds, tomato seeds, pumpkin seeds, almond, hazelnut, nut, evening primrose, borage, safflower, false flax, oil poppy, macroalgae, microalgae, and microorganisms, and mixtures thereof, and cocoa butter, illipe butter, rhea butter, and mixtures thereof.

12. A method according to claim 1, wherein the first solvent system comprises of a fluorinated aromatic solvent, a tert-butyl ether, a solvent comprising at least one silicon atom, or methyl-tetrahydrofuran (MeTHF).

13. A method according to claim 1, wherein the first solvent system consists of a first solvent selected from fluorinated aromatic solvents, tert-butyl ethers, solvents comprising at least one silicon atom, and methyl-tetrahydrofuran (MeTHF), and a second solvent, not identical to the first, selected from fluorinated aromatic solvents, tert-butyl ethers, solvents comprising at least one silicon atom, and methyl-tetrahydrofuran (MeTHF).

14. A method according to claim 1, wherein the first solvent system consists of one or more solvents selected from hexamethyldisiloxane (HMDS), hexafluorobenzene (BHF) and trifluorotoluene (BTF), methyl-tetrahydrofuran (MeTHF), methyl tert-butyl ether (MTBE), ethyl-tert-butyl-ether (ETBE) and tetramethylsilane (TMS).

15. A method according to claim 1, wherein the first solvent system consists of hexamethyldisiloxane (HMDS) and methyl-tetrahydrofuran (MeTHF).

16. A method according to claim 1, wherein the first solvent system consists of ethyl-tert-butyl-ether (ETBE).

17. A method according to claim 1, wherein the unsaponifiable obtained is selected from a soya unsaponifiable, an avocado unsaponifiable, a furan fraction-rich avocado unsaponifiable and/or a sterol fraction-rich avocado unsaponifiable, or a mixture of avocado and soya unsaponifiables (ASU).

* * * * *